US009824164B2

(12) United States Patent
Bohbot et al.

(10) Patent No.: US 9,824,164 B2
(45) Date of Patent: Nov. 21, 2017

(54) SYSTEM AND METHOD OF PREDICTING POLLUTANT EMISSIONS OF A VEHICLE WITH SIMULTANEOUS CHEMICAL KINETICS AND EMISSIONS CALCULATIONS

(71) Applicant: IFP Energies nouvelles, Rueil-Malmaison (FR)

(72) Inventors: Julien Bohbot, Verrieres le Buisson (FR); Anthony Velghe, Rueil-Malmaison (FR)

(73) Assignee: IFP ENERGIES NOUVELLES, Rueil-Malamaison (FR)

( * ) Notice: Subject to any disclaimer, the term of this patent is extended or adjusted under 35 U.S.C. 154(b) by 618 days.

(21) Appl. No.: 13/711,865

(22) Filed: Dec. 12, 2012

(65) Prior Publication Data
US 2013/0158967 A1    Jun. 20, 2013

(30) Foreign Application Priority Data

Dec. 20, 2011 (FR) ...................... 11 03991

(51) Int. Cl.
*G06F 7/60* (2006.01)
*G06G 7/48* (2006.01)
(Continued)

(52) U.S. Cl.
CPC ..... *G06F 17/5009* (2013.01); *F02D 41/1444* (2013.01); *F02D 41/266* (2013.01);
(Continued)

(58) Field of Classification Search
CPC .. G06F 19/702; G06F 19/709; G06F 17/5009; F02D 41/1444; F02D 41/266; F02D 2250/12
(Continued)

(56) References Cited

U.S. PATENT DOCUMENTS 8,495,090 B2    7/2013 Onodera
2007/0294581 A1* 12/2007 Dean ...................... G06F 9/5027
714/33
(Continued)

FOREIGN PATENT DOCUMENTS

JP    2005-249420 A    9/2005
JP    2008-198025 A    8/2008

OTHER PUBLICATIONS

Bohbot J. Et Al., "IFP-C3D: An Unstructured Parallel Solver for Reactive Compressible Gas Flow with Spray", May 1, 2009, Oil & Gas Science and Technology—Revue De L'institut Francais Du Petrole, vol. 64. No. 3. pp. 309-335.*
(Continued)

*Primary Examiner* — Juan Ochoa
(74) *Attorney, Agent, or Firm* — Fitch, Even, Tabin & Flannery LLP

(57) ABSTRACT

The invention is a system for predicting emissions of pollutants from a vehicle equipped with an engine using processors (3) to determine emission of pollutants. The processors include a first group of processors (1) for carrying out calculations of chemical kinetics for determining the amounts of chemical compounds present in a chemical reaction in the engine and a second group of processors (2) for carrying out calculations of emission of pollutants simultaneously with the calculation of chemical kinetics, allowing determination of the emission of pollutants from the calculated amounts of chemical compounds. The first group of processors (1) has a global supervisor processor (4) allowing storing data required for the calculations and to distribute the calculations to clusters (5) of processors.

23 Claims, 2 Drawing Sheets

(51) Int. Cl.
G06F 17/50 (2006.01)
G06F 19/00 (2011.01)
F02D 41/14 (2006.01)
F02D 41/26 (2006.01)

(52) U.S. Cl.
CPC ........ G06F 19/702 (2013.01); *F02D 2250/12* (2013.01); *G06F 19/709* (2013.01)

(58) Field of Classification Search
USPC ........................................................ 703/2, 8
See application file for complete search history.

(56) References Cited

U.S. PATENT DOCUMENTS

2008/0192653 A1    8/2008  Onodera
2009/0171631 A1*   7/2009  Dweik ................ G06F 17/5009
                                                    703/2

OTHER PUBLICATIONS

Bohbot Et Al., (Bohbot(1) hereinafter), A Multi-Dimensional Spatial Scheme for Massively Parallel Compressible Turbulent Combustion Simulation, Jun. 14-17, 2010, V European Conference on Computational Fluid Dynamics—ECCOMAS CFD, pp. 1 20.*
Feichtinger et al., "Concepts of waLBerla prototype 0.1", 2007, Univ. of Erlangen, pp. 1-28.*
Richard M. Fujimoto, Parallel and Distributed Simulation, 1999, Proceedings of the 1999 Winter Simulation Conference, pp. 122-131.*
Richard M. Fujimoto, "Parallel discrete event simulation", 1990, Communications of the ACM 33.10, pp. 30-53.*
Donath et al., "waLBerla: The Need for Large-Scale Super Computers", 2007, High Performance Computing in Science and Engineering, Garching/Munich 2007, Springer Berlin Heidelberg, 2009, pp. 459-473.*
Feichtinger et al., "WaLBerla: HPC software design for computational engineering simulations", 2011, Journal of Computational Science 2.2, pp. 105-112.*
Feichtinger et al., "WaLBerla: Exploiting massively parallel systems for lattice Boltzmann simulations", 2009, Parallel Computing, Springer London, pp. 241-260.*
Sims et al. "Accelerating scientific discovery through computation and visualization", 2000, Journal of Research of the National Institute of Standards and Technology 105.6: 875, pp. 1-24.*
Ebrahimian et al., "Second Generation Tools for the Modelling of Diesel Engine mixture preparation", 2010, SIA 2010, Rouen, France, pp. 1-9.*
Lovas et al., "Unified development solution for cluster and grid computing and its application in chemistry", 2004, Computational Science and Its Applications-ICCSA, pp. 226-235.*
Knop et al., "Modelling of combustion and nitrogen oxide formation in hydrogen-fuelled internal combustion engines within a 3D CFD code", 2008, International Journal of Hydrogen Energy 33.19, pp. 5083-5097.*
Bohbot and Gillet, "Impact of different mesh remapping techniques on 3D simulations in internal combustion engines", 2006, European Conference on Computational Fluid Dynamics ECCOMAS CFD, pp. 1-20.*
Bohbot et al., A new coupling approach using a 1D system simulation software and a 3D combustion code applied to transient engine operation, 2004, No. 2004-01-3002, SAE Technical Paper, pp. 1-13.*
Bohbot et al., "Multiscale Engine Simulations using a Coupling of 0-D/1-DModel with a 3-D Combustion Code", 2009, Oil & Gas Science and Technology-Revue de l'IFP 64.3, pp. 337-359.*
Japanese Search Report dated Dec. 27, 2016 issued against Japanese Patent Application No. 2012-276813 [including English translation].
J. Bohbot et al., "IFP-C3D: an Unstructured Parallel Solver for Reactive Compressible Gas Flor with Spray", Oil & Gas Science and Technology, vol. 64, No. 3, (2009), pp. 309-335.

* cited by examiner

SYSTEM AND METHOD OF PREDICTING POLLUTANT EMISSIONS OF A VEHICLE WITH SIMULTANEOUS CHEMICAL KINETICS AND EMISSIONS CALCULATIONS

CROSS REFERENCE TO RELATED APPLICATION

Reference is made to French Patent Application No. 11/03.991, filed on Dec. 20, 2011, which application is incorporated herein by reference in its entirety.

BACKGROUND OF THE INVENTION

Field of the Invention

The present invention relates to simulation of pollution emission of pollutants from vehicles and notably motor cars.

Description of the Invention

The economic and environmental constraints regarding fuel consumption and emission of pollutants are increasingly restrictive for car manufacturers. For example, the EURO standard defining the maximum limit for emission of vehicle pollutants ($CO_2$, NOx, soots, unburnt hydrocarbons and particles) is becoming increasingly restrictive. Manufacturers therefore want to optimize their vehicles in order to minimize emission of pollutants Simulations of emissions are therefore increasingly used in order to predict the engine behavior without requiring numerous and long experimental measurements.

In order to predict vehicle emissions, the post-oxidation phase (i.e. oxidation of the gases by a diffusion flame) in the combustion chamber is simulated using a FPI (Flame Prolongation of Intrinsic Low Dimensional Manifold) chemical kinetics tabulation method. The tables used for this type of model are generated from a computer code solving the chemical kinetics, such as, for example, the Chemkin® software developed by Reaction Design®. This tabulation details the molar amounts of all the chemical compounds present in a reaction, according to a given reaction scheme and to thermodynamic conditions. These tables are then used for calculation of the emission of pollutants by a CFD computer program (Computational Fluid Dynamics) type, such as, notably for example, IFP-C3D® software developed by IFP Energies nouvelles.

This solution however involves several drawbacks. First, the tabulation methods have to account for the thermodynamic and chemical path, which is very complex for engine modelling. In order to overcome this problem, additional variables have to be introduced in the tables. This increasing number of parameters leads to an increase in the size of the chemical tables, which entails the production of tables occupying a very large physical memory space. Furthermore, when the tables are generated, some physical hypotheses, notably on the type of chemical reactor used (that is, the enclosure where the chemical reaction occurs), are made. The tables that are generated assume that chemical reactors having constant volumes are unusable in the case of variable-volume reactors. This first selection is fundamental for the simulation of variable-geometry combustion chambers. However, during engine cycles, reality can come close to one hypothesis, then to the next. Simulation results can therefore be imprecise or even erroneous.

In order to overcome these difficulties, developing a direct coupling between the two calculation codes, the IFP-C3D® and Chemkin® softwares for example, has been considered for simulating the burnt gas post-oxidation phase. According to this method, during direct coupling, the composition of the mixture and the terms concerning the chemical sources are calculated during the emissions calculation. When the emissions calculation code is executed, the composition of the mixture is evaluated by direct calculation of the chemical kinetics from the given local thermodynamic conditions. The emissions calculation part receives the chemical results and incorporates them in the equations. Simulation can thus be continued. Knowledge of the thermodynamic path is therefore no longer necessary, which simplifies chemical modelling.

However, direct coupling requires a chemical kinetics calculation for each time iteration and for all the cells that burn which leads to additional calculation costs that have to be reduced as much as possible to make the use thereof compatible with industrial constraints.

SUMMARY OF THE INVENTION

The present invention allows prediction of the emissions from a vehicle equipped with a combustion engine by carrying out the chemical kinetics calculations simultaneously with the emissions calculations, the kinetics calculations are distributed, then carried out simultaneously by processors, which is enabled by a parallel architecture of the computing processors. The system according to the invention allows automatic management of the distribution of the chemical kinetics calculations.

The invention relates to a system for predicting the emission of pollutants of a vehicle equipped with an engine, comprising processors for determining the emission of pollutants, comprising:

a first group of processors for carrying out calculation of chemical kinetics which allows determination of amounts of chemical compounds present in a chemical reaction in the engine according to a given reaction scheme and to the thermodynamic conditions of the engine, a second group of processors for carrying out the calculation of emission of pollutants which allows determination of the emission of pollutants from the calculation of amounts of the chemical compounds; and wherein
the calculations of the two groups of processors are carried out simultaneously.

The first group of processors comprises a global supervisor processor and of at least one cluster of processors. The global supervisor processor provides storage of data required for calculation and distributes the calculations among the available at least one cluster of processors.

According to the invention, the at least one cluster of processors includes a local supervisor processor and of at least one slave processor. The local supervisor processor stores data and distributes calculations among the slave processors. Each slave processor is able to carry out calculations of chemical kinetics for a portion of the model of the engine.

The system comprises first communication means between the two groups of processors which provide transfer of the data resulting from the calculations of emission of pollutants to the first group of processors and the results of the calculation of chemical kinetics to the second group of processors.

Furthermore, the system comprises second communication means between the global supervisor and the at least one processor cluster, which allows transfer of the data required for the calculations from the global supervisor to the at least one cluster and the results of the simulations from the at least one cluster to the global supervisor.

Advantageously, the system comprises third communication means between the local supervisors and the slave processors which allows transfer of the data required for simulation from the local supervisor to the slave processors and the results of the calculations from the slave processors to the local supervisor.

Preferably, the calculations of chemical kinetics are carried out by chemical kinetics software executed by the first group of processors and with the calculations of emission of pollutants which are carried out by software executed by the second group of processors.

According to a preferred embodiment of the invention, coupling the calculations of the two groups of processors uses a message passing interface MPI.

Advantageously, the communication means are achieved from functions selected in a function library of the MPI interface.

Preferably, each group of processors comprises a global communicator.

Advantageously, each cluster of processors comprises a chemistry communicator.

The invention also relates to a method of predicting the pollution emission of pollutants from of a vehicle, comprising the following stages:

carrying out calculations of chemical kinetics allowing determination of amounts of chemical compounds present in a chemical reaction in the engine according to a given reaction and to thermodynamic conditions of the engine, calculating emission of pollutants allows determination of emission of pollutants from the calculated amounts of chemical compounds.

For this method, calculations of chemical kinetics are carried out simultaneously.

The method is preferably implemented by the system as described above.

BRIEF DESCRIPTION OF THE FIGURES

Other features and advantages of the method according to the invention will be clear from reading the description hereafter of embodiments given by way of non limitative example, with reference to the accompanying figures wherein.

DETAILED DESCRIPTION

The invention relates to a computer system for predicting emissions of pollutants from a vehicle comprising processors dedicated to determining the emissions. The computer system furthermore comprises:

a first group of processors for carrying out calculations of chemical kinetics allowing determination of amounts of all the chemical compounds present in a chemical reaction in a cylinder of an engine of the vehicle according to a reaction scheme and to thermodynamic conditions of the engine;

a second group of processors for carrying out calculations of emission of pollutants allows determination of the emission of pollutants from calculated amounts of the chemical compounds; and wherein the calculations by groups of processors are carried out simultaneously.

Figure 1:
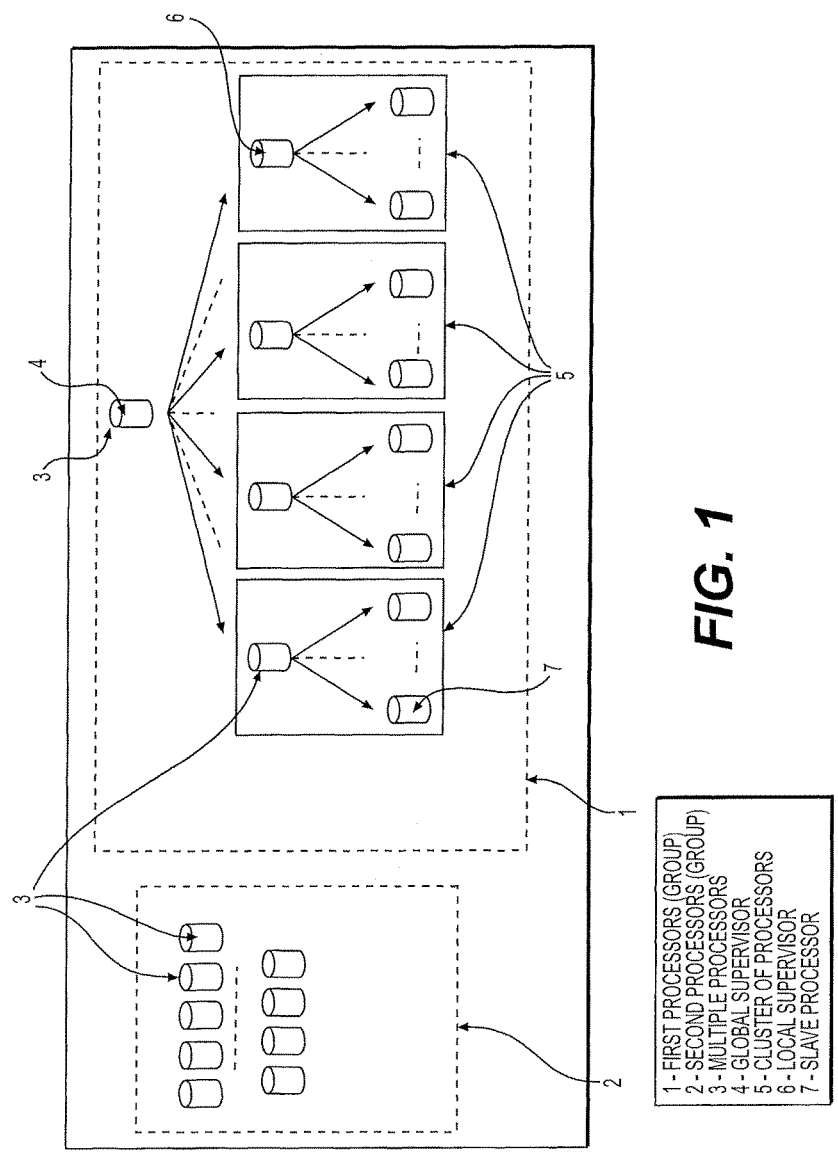
FIG. 1 illustrates the global architecture of the computer system according to the invention.

FIG. 1 illustrates the global structure of the computer system according to the invention. The system has a parallel structure enabled by the parallel architecture of the new calculators. Thus, the calculations of chemical kinetics are carried out during the calculations of emissions. The post-oxidation simulation time is thus reduced.

In order to implement the coupling between the two calculation codes, the system according to the invention comprises a parallel architecture allowing automatic distribution of the calculations of chemical kinetics calculations among multiple processors (3) at a time.

This architecture first separates the processors dedicated to simulation into two groups 1 and 2. The first group (1) is dedicated to carrying out calculation of chemical kinetics. The calculation of chemical kinetics allows determination of molar amounts of all the chemical compounds present in a chemical reaction in the engine of the vehicle according to a given reaction scheme and to the thermodynamic conditions of the engine. The second group (2) is reserved for the execution of code performing calculation of the emission of pollutants code. These calculations allow determination of the emissions of pollutants from the simulated molar amounts of the chemical compounds. Each calculation part is thus carried out by processors that are exclusively reserved therefor.

The first group of processors 1 is then divided into clusters of processors 5. Indeed, the first group of processors 1 comprises a processor referred to as global supervisor 4 and clusters of processors 5. The function of global supervisor 4 is to receive the parallel information from the second group of processors 2 and to distribute the calculations among the various clusters 5 to optimize the computation time.

According to a preferred embodiment, a local supervisor is arranged within a cluster of processors 5 to receive information from global supervisor 4 of the calculations from slave processors included in cluster of processors 5.

This type of architecture allows the calculation of chemical kinetics to be distributed among a large number of processors grouped into clusters in order to reduce the computation times. On the other hand, the two levels of supervisors 4 and 6 allows limitation of effects referred to as funnel effects when the data calculated are sent to the end of calculation and to automate the distribution of the calculation load among the various slave processors 7.

Supervisors 4 and 6 distribute the calculations respectively among the clusters of processors 5 and the slave processors that are available to carry out calculations. These are, on the one hand, the clusters having at least one available slave processor and, on the other hand, the slave processors that are not allocated to the execution of a calculation. Thus, the calculations are homogeneously distributed among processors 3.

Figure 2:
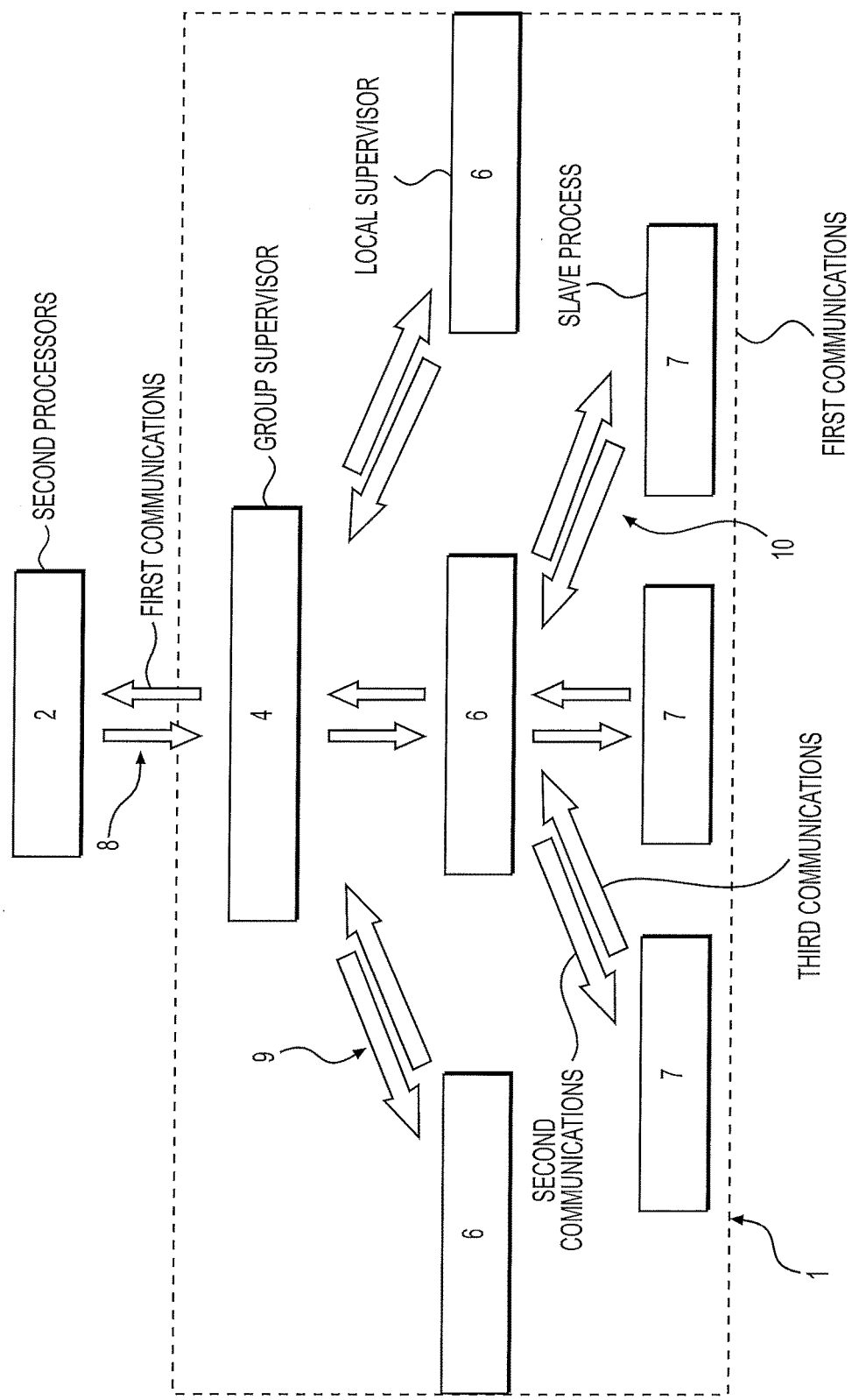
FIG. 2 illustrates the architecture of the first group of processors dedicated to the calculation of chemical kinetics according to the invention.

FIG. 2 illustrates the structure of the first group of processors with notably a representation of the data exchanges between the various components of the system according to the invention.

At each time iteration, data resulting from the calculation of emission of pollutants are sent to global supervisor 4 by first communication means 8 arranged between the two groups of processors 1 and 2. Global supervisor 4 receives the parameters for carrying out the calculation of chemical kinetics and distributes these data automatically among the various clusters of processors 5 that are available (on which no calculation is being executed) by a second communication means 9. The local supervisors 6 of clusters of processors 6 distribute the calculations among the slave processors which are available by a third communication means 10. Each local supervisor 6 sends to each slave processor 7 a data set containing the parameters of a zone of a model of the simulated engine. As soon as a slave processor 7 completes its calculation, it sends the chemistry calculation result to local supervisor 6 through third communication means 10. Local supervisor 6 stores the result, then sends to the slave processor 7 the parameters concerning another zone of the model of the engine to be simulated. The algorithm is completed when a chemistry calculation has been carried out on the entire engine model that is all the zones of the model from the emissions code for calculating emissions.

Preferably, the code for making calculations which is dedicated to calculations of emissions of pollutants uses a meshed model of the engine combustion chamber. Thus, a zone of the engine model simulated by a slave processor corresponds to a cell or to a parcel of cells of this model.

This calculation distribution method promotes good load balancing among all the processors. This therefore allows reduction of the post-oxidation simulation time.

In a preferred embodiment, direct coupling of the calculations of emissions of pollutants and of the calculations of chemical kinetics is implemented in the Fortran programming language, preferably in Fortran 90. The direct coupling can advantageously use the library of the MPI interface (Message Passing Interface) to allow distribution of the parallel calculations which reduces the code execution time. The two calculation codes are distinct and dynamic allocation of the processors is achieved.

The MPI interface is a standard defining a function library, usable with the C and Fortran languages. It allows exploitation of remote computers or multiprocessors through message passing. This technique is commonly used for executing parallel programs on distributed memory systems.

The MPI interface affords the advantage of obtaining good performances whether with shared-memory massively parallel machines or heterogeneous distributed-memory computer assemblies. Moreover, it is available in a very large range of processing materials and systems. This interface thus affords the advantage, in relation to other message passing libraries, of being widely portable. It has been set up on almost all the memory architectures and it is fast because each setup has been optimized for the material on which it executes its tasks.

When using this interface, a set of processes that can communicate with one another is referred to as a communicator, and two processes can communicate only if they are in the same communicator. An initial communicator encompasses all the processes (MPI_COMM_WORLD) that can be subdivided into smaller communicators corresponding to logical entities. There are two types of communicators which are intracommunicators and intercommunicators. Intracommunicators are the standard communicators, whereas intercommunicators are used for creating a bridge between two intracommunicators.

Thus, according to the invention, dividing the processors 1 and 2 into two groups is performed by the MPI_COMM_SPLIT function included in the function library of the MPI interface. The processors dedicated to the calculation of emissions of pollutants 2 are included in the global communicator space 2 for calculation of emissions and those dedicated to the chemistry calculations 1 are included in the global communicator space 1 for calculation of chemical kinetics calculation. MPI communications are created between these two spaces which correspond to first communication means 8 described above.

According to the invention, the chemical kinetics calculation communicator 1 is subdivided into a global supervisor 4 and at least one chemistry communicator 5 with each chemistry communicator 5 corresponding respectively to a cluster of processors 5. In each chemistry communicator 5, there is a local supervisor 6 that receives information from global supervisor 4 that itself distributes the calculations among slave processors included in its communicator.

Two types of communication between the various communicators and within a single communicator are necessary to distribute the data. On the one hand, the inter-communicator communications allows communication from one communicator to the next. For example, an inter-communicator communication 9 corresponding to second communication means 9 is created between global supervisor 4 and each local supervisor 6 of the chemistry communicator 5 by the MPI_INTER_COMM_CREATE function of the function library of the MPI interface. On the other hand, intra-communicator communications 10 corresponding to third communication means 10 exchange data between a local supervisor 6 and a slave processor 7 within a communicator 5. Data transfers are achieved by means of point-to-point or collective MPI communications (MPI_BCAST function of the function library of the MPI interface for example).

Point-to-point communications allow two processes within a single communicator to exchange a datum in scalar, chart or derivative type form. The corresponding functions of the library of the MPI interface are MPI_SEND, MPI_RECV and MPI_SENDRECV.

Collective communications involve all the processes of a communicator. It is possible to send a single datum to all the processes (MPI_BCAST), to partition a chart between all the processes (MPI_SCATTER) or to carry out an operation (an addition for example) to which each process contributes.

Preferably, the code used for the calculation of emissions of pollutants is a CFD (Computational Fluid Dynamics) type program, and the IFP-C3D® software developed by IFP Energies nouvelles can notably be used. By means of this software, three-dimensional (3D) simulation is used to calculate the two-phase flows (gas/liquid fuel) reactive in internal-combustion engines. This software allows analysis of the complex physical phenomena that occur in engines (flooding linked with short-circuiting involved by valve overlap, liquid film formation of the walls, pollutant formation, etc.). For the chemical kinetics calculations, the Chemkin® software developed by Reaction Design® can be used. This software is able to solve a large number of chemical reaction combinations in order to understand a complex problem and it is therefore suited to this issue.

The invention also relates to a prediction of emissions of pollutants method wherein the following stages are carried out:

carrying out calculations of chemical kinetics, allowing determination of the amounts of chemical compounds present in a chemical reaction in the engine according to a given reaction scheme and to the thermodynamic conditions of the engine, simultaneously carrying out calculations of emissions of pollutants allowing determination of emission of pollutants from the calculated amounts of chemical compounds.

For the method according to the invention, chemical kinetics calculations are carried out simultaneously.

Advantageously, the method is implemented by the system as described above.

The invention claimed is:

1. A system for predicting emissions of pollutants from a vehicle equipped with an engine, including processors for determining the emissions of pollutants, comprising:
a first group of processors which perform calculations of chemical kinetics which determine amounts of chemical compounds present in a chemical reaction in the engine according to a reaction and to thermodynamic conditions of the engine;
a second group of processors which perform calculations of the emissions of pollutants from determined amounts of the chemical compounds;
the calculations of chemical kinetics by the first group of processors are carried during calculations of emissions of pollutants by the second group of processors;
the first group of processors comprises a global supervisor processor and at least one cluster of processors and the global supervisor processor stores data which is used to perform the calculations of chemical kinetics and distributes the calculations of chemical kinetics among available processors of the at least one cluster of processors; and
first communication means connecting the first and the second groups of processors which transfers data resulting from the calculations of chemical kinetics by the first group of processors and transfers data from the calculations of the emissions of pollutants by the second group of processors.

2. A system as claimed in claim 1, wherein:
the at least one cluster of processors comprises a local supervisor processor and at least one slave processor and the local supervisor processor stores data and distributes the calculations of chemical kinetics among at least one slave processor with each slave processor carrying out calculations of chemical kinetics for a portion of a model of the engine.

3. A system as claimed in claim 1, comprising:
second communication means connecting the global supervisor and the at least one cluster of processors which transfers data required for calculations by the global supervisor to the at least one cluster of processors and which transfers results of simulations from the at least one cluster of processors to the global supervisor.

4. A system as claimed in claim 2, wherein the system comprises:
second communication means connecting the global supervisor and the at least one cluster of processors which transfers data required for calculations by the global supervisor to the at least one cluster of processors and which transfers results of simulations from the at least one cluster of processors to the global supervisor.

5. A system as claimed in claim 1, comprising:
third communication means connecting a local supervisor processor and the at least one slave processor which transfers data required for simulation by the local supervisor processor to the at least one slave processor and which transfers results of calculations from the at least one slave processor to the local supervisor processor.

6. A system as claimed in claim 1, comprising:
software, executable by the first group of processors, for calculating the chemical kinetics.

7. A system as claimed in claim 2, comprising:
software, executable by the first group of processors, for calculating the chemical kinetics.

8. A system as claimed in claim 3, comprising:
software, executable by the first group of processors, for calculating the chemical kinetics.

9. A system as claimed in claim 5, comprising:
software, executable by the first group of processors, for calculating the chemical kinetics.

10. A system as claimed in claim 1, comprising:
software, executable by the second group of processors, for calculating the emissions of pollutants.

11. A system as claimed in claim 2, comprising:
software, executable by the second group of processors, for calculating the emissions of pollutants.

12. A system as claimed in claim 3, comprising:
software, executable by the second group of processors, for calculating the emissions of pollutants.

13. A system as claimed in claim 5, comprising:
software, executable by the second group of processors, for calculating the emissions of pollutants.

14. A system as claimed in claim 6, comprising:
software, executable by the second group of processors, for calculating the emissions of pollutants.

15. A system as claimed in claim 1, comprising:
a message passing interface for coupling calculations between the first and second groups of processors.

16. A system as claimed in claim 2, comprising:
a message passing interface for coupling calculations between the first and second groups of processors.

17. A system as claimed in claim 3, comprising:
a message passing interface for coupling calculations between the first and second groups of processors.

18. A system as claimed in claim 5, comprising:
a message passing interface for coupling calculations between the first and second groups of processors.

19. A system as claimed in claim 6, wherein:
a message passing interface for coupling calculations between the first and second groups of processors.

20. A system as claimed in claim 1, comprising:
a message passing interface, including a library of selectable functions, for providing a function of at least one communication means; and wherein
the function of the at least one communication means is provided from the library of selectable functions.

21. A system as claimed in claim 20, wherein:
the first and second groups of processors comprise a global communicator.

22. A system as claimed in claim 20, wherein:
each cluster of processors comprises a chemistry communicator.

23. A method for predicting emissions of pollutants from an engine of a vehicle which is performed by a system for predicting the emissions of pollutants, comprising:
calculating chemical kinetics used for determining amounts of chemical compounds present in chemical reactions in the engine according to the chemical reactions and thermodynamic conditions of the engine; and
carrying out calculations of chemical kinetics during the calculations of emissions of pollutants and the calculations of chemical kinetics and the calculations of emissions of pollutants are used for predicting the emissions of pollutants from the determining amounts of the chemical compounds, and wherein
a first group of processors performs the calculations of chemical kinetics which determine the amounts of chemical compounds present in the chemical reactions in the engine according to the chemical reactions and the thermodynamic conditions of the engine;

a second group of processors performs the calculations of the emissions of pollutants from the determined amounts of the chemical compounds;

the calculations of chemical kinetics by the first group of processors are carried out during the calculations of the emissions of pollutants by the second group of processors; and the first group of processors comprises a global supervisor processor and at least one cluster of processors and the global supervisor processor stores data required for the calculations of chemical kinetics and distributes the calculations of chemical kinetics among available processors of the at least one cluster of processors.

* * * * *